(12) United States Patent
Umemoto

(10) Patent No.: US 10,918,531 B2
(45) Date of Patent: Feb. 16, 2021

(54) ABSORBENT ARTICLE

(71) Applicant: DAIO PAPER CORPORATION, Ehime (JP)

(72) Inventor: Kaori Umemoto, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 419 days.

(21) Appl. No.: 15/514,451

(22) PCT Filed: Sep. 28, 2015

(86) PCT No.: PCT/JP2015/077340
§ 371 (c)(1),
(2) Date: Mar. 24, 2017

(87) PCT Pub. No.: WO2016/052415
PCT Pub. Date: Apr. 7, 2016

(65) Prior Publication Data
US 2017/0281421 A1    Oct. 5, 2017

(30) Foreign Application Priority Data

Sep. 30, 2014   (JP) .................................. 2014-200550

(51) Int. Cl.
*A61F 13/49* (2006.01)
*A61F 13/53* (2006.01)
*A61F 13/534* (2006.01)

(52) U.S. Cl.
CPC ........ *A61F 13/49001* (2013.01); *A61F 13/49* (2013.01); *A61F 13/49007* (2013.01); *A61F 13/53* (2013.01); *A61F 13/534* (2013.01)

(58) Field of Classification Search
CPC ................ A61F 13/49; A61F 13/49001; A61F 13/49007; A61F 13/53; A61F 13/534
See application file for complete search history.

(56) References Cited

U.S. PATENT DOCUMENTS

| | | | |
|---|---|---|---|
| 5,611,790 A * | 3/1997 | Osborn, III | A61F 13/472 604/373 |
| 2008/0140042 A1* | 6/2008 | Mukai | A61F 13/49001 604/385.23 |
| 2013/0102982 A1* | 4/2013 | Nakano | A61F 13/49019 604/365 |

FOREIGN PATENT DOCUMENTS

| | | |
|---|---|---|
| CN | 103260570 A | 8/2013 |
| JP | 1988-031265 U | 9/1989 |
| JP | H0428363 A | 1/1992 |
| JP | H11332913 A | 12/1999 |
| JP | 2002035029 A | 2/2002 |

(Continued)

*Primary Examiner* — Kai H Weng
(74) *Attorney, Agent, or Firm* — Muncy, Geissler, Olds & Lowe, PC

(57) ABSTRACT

The present invention is intended to improve the liquid diffusibility and fit of an absorber having a first slit extending in a front-back direction and second slits continuing laterally from the first slit to the side edges. The foregoing issue is solved by providing one first slit extending in the front-back direction in a width-direction intermediate portion of an absorber, providing second slits continuing from each of front end side and back end side of the first slit toward width-direction both sides to the side edges, and providing second slit elastic members to cross in the direction of continuance of the second slits and exert a contraction force in the direction of closing of the second slits.

5 Claims, 16 Drawing Sheets

(56) References Cited

FOREIGN PATENT DOCUMENTS

| | | | |
|---|---|---|---|
| JP | 2002178428 | A | 6/2002 |
| JP | 2002273808 | A | 9/2002 |
| JP | 2004141270 | A | 5/2004 |
| JP | 2006149571 | A | 6/2006 |
| JP | 2008183160 | A | 8/2008 |
| JP | 2012115464 | A | 6/2012 |
| JP | 2012143535 | A | 8/2012 |
| JP | 2013078369 | A | 5/2013 |

* cited by examiner

ABSORBENT ARTICLE

TECHNICAL FIELD

The present invention relates to an absorbent article including an absorber with a slit.

BACKGROUND ART

Absorbent articles including disposable diapers, sanitary napkins, and others include an absorber for absorbing urine, feces, menstrual blood, or the like. The absorber is known to be manufactured by a fiber stacking apparatus 101 as illustrated in FIG. 15, for example. Specifically, the fiber stacking apparatus 101 includes a defibrating device 104 that finely crushes a raw pulp sheet 100, a crushed pulp supply casing 108 surrounding the defibrating device 104, and a fiber stacking drum 110 disposed at the downstream-side opening part of the crushed pulp supply casing 108.

The crushed pulp supply casing 108 constitutes the exterior of a chamber C for delivering the crushed pulp by flowing air to the outer peripheral surface of the downstream fiber stacking drum. The crushed pulp supply casing 108 is provided with a polymer supply port 106 for supplying absorbent polymer P separately from the crushed pulp in the chamber C.

The fiber stacking drum 110 also has air-permeable absorber formation concave portions with a fine mesh on one surface or a large number of microscopic pores on one surface, formed at appropriate intervals on the outer peripheral surface. The inside of the fiber stacking drum 110 is kept under negative pressure (the part shown by symbol (−) in the drawing) by an absorbing means not illustrated such that the crushed pulp air-conveyed into the absorber formation concave portions is mixed with the absorbent polymer and stacked. The absorber 13 formed on the fiber stacking drum 110 is transferred onto the upper surface of a package sheet 14 conveyed on a vacuum conveyor by turning the inside of the fiber stacking drum 110 into positive pressure (the part shown by symbol (+) in the drawing) and sucking the absorber 13 by a vacuum device 149, and are conveyed on the conveyor and sent to a downstream processing step.

The absorber in the absorbent article is known to have a slit extending in a front-back direction (this refers to a narrow clearance penetrating through the absorber in a thickness direction, which is applied to the following description) in a width-direction intermediate portion to improve absorbing performance or leakage prevention performance (for example, refer to Patent Documents 1 and 2). The absorber having such a slit has been conventionally manufactured in such a manner that the fiber stacking drum is processed by press molding or welding of another member to have convex portions protruding toward the outer peripheral surface of the drum at a slit forming position in the absorber formation concave portion fiber stacking drum to suppress the stack of the fiber in the convex portions and stack the fiber in the surrounding areas of the convex portions. However, according to the method by which to form the convex portions in the absorber formation concave portions, it is necessary to modify the fiber stacking drum at the time of change of the slit pattern. This causes the problems that the cost will increase and various kinds of products cannot be manufactured simply by changing the slit pattern on the same fiber stacking drum.

As a solution to the problems, there is a technique by which to attach a mask 120 shaped as illustrated in FIG. 16 to the outer peripheral surface of the fiber stacking drum 110 without modifying the fiber stacking drum. The dot-and-dash lines in the drawing indicate the boundaries between the individual absorbers. According to this technique, no fiber is stacked on the part covered by the mask 120 to form the slit. The mask 120 needs to have a main slit pattern 121 for forming a first slit extending in the front-back direction on the width-direction intermediate portion of the absorber formation concave portions and auxiliary patterns 122 extending from the main slit pattern 121 to the lateral sides of the absorber formation concave portions.

In this technique, however, the auxiliary patterns 122 extending from the main slit pattern 121 to the lateral sides of the absorber formation concave portions are necessary to lift and support the main slit pattern 121. Accordingly, the absorber does not have only the first slit resulting from the main slit pattern 121 but also second slits resulting from the auxiliary patterns 122 continuing from the first slit to the side edges of the absorber. Even though the second slits resulting from the auxiliary patterns 122 are made narrow, the second slits exert influence on the liquid diffusibility (the slits facilitate the diffusion of liquid in the slit extending direction and inhibit the diffusion of liquid in the direction crossing the slit extending direction, which may cause lateral leakage) and exert influence on the fit due to deformation (the slits are likely to fold along the slit extending direction). It is desired to resolve these problems satisfactorily.

CITATION LIST

Patent Documents

Patent Document 1: JP-A No. 2008-183160
Patent Document 2: JP-A No. 2006-149571

SUMMARY OF INVENTION

Technical Problem

A major object of the present invention is to improve the liquid diffusibility and fit of an absorber having a first slit extending in the front-back direction and second slits continuing laterally from the first slit to the side edges.

Solution to Problem

The present invention having solved the foregoing problems is as follows:
<The Invention of Claim 1>
A disposable diaper, wherein an absorbent article includes an absorber, the absorber has a first slit formation region in a width-direction intermediate portion where one or more first slits extending in a front-back direction are provided at width-direction intervals, the absorber has second slits continuing from each of front end side and back end side of the first slit formation region toward width-direction both sides to the side edges, and the absorbent article has second slit elastic members that cross in the continuous direction of the second slits and exert a contraction force in the direction of closing of the second slits.
(Operation and Effect)
In the absorber of the present invention, when the second slits are partially or completely closed by the contraction force of the second slit elastic members to shorten the front-back direction length of the width-direction both sides of the first slit formation region, the absorber is folded along the first slit formation region and is deformed into an almost boat shape. Therefore, the second slits are narrower or the both sides of the second slits are brought into contact with each other to enhance the liquid diffusibility in the direction crossing the second slits and suppress the liquid diffusion in the direction along the second slits, thereby preventing lateral leakage in an effective manner. In addition, the absorber is deformed into a boat shape as a whole by combination of deformations of the first slit and the second slits to provide a fit and leakage prevention in an effective manner.

<The Invention of Claim 2>

The disposable diaper according to claim 1, wherein the first slit formation region is composed of the two first slits provided at a width-direction interval, and the second slits include ones continuing from the first slit on one side in the width-direction to the side edge of the absorber on one side in the width-direction and ones continuing from the first slit on the other side in the width-direction to the side edge of the absorber on the other side in the width-direction.

(Operation and Effect)

Providing the two first slits allows the regions of the second slits to rise with respect to the region between the first slits to turn the absorber into a boat shape. This further improves a fit.

<The Invention of Claim 3>

The disposable diaper according to claim 1 or 2, including a cross-linkage slit linking the two first slits in the width direction, wherein the sum total of clearance width of the cross-linkage slit is smaller than the sum total of clearance width of the second slits.

(Operation and Effect)

Providing the cross-linkage slit allows linkage of the two first slits and the second slits on the width-direction both sides of the first slits. In the mask at the time of manufacture described above, the main slit pattern can be supported from the width-direction both sides via the auxiliary slit pattern (the pattern for forming the second slits and the cross-linkage slit), which allows the main slit pattern to be supported more firmly. In addition, the sum total of the clearance width of the cross-linkage slit is set to be small to make the absorber likely to be turned into a boat shape described above.

<The Invention of Claim 4>

The disposable diaper according to any one of claims 1 to 3, wherein three-dimensional gathers rising toward the wearer's skin are extended on the width-direction both sides of the surface from the ventral side to the dorsal side, the three-dimensional gathers have three-dimensional gather elastic members extending in the front-back direction, and at least portions of the three-dimensional gather elastic members crossing the second slits serve as the second slit elastic members.

(Operation and Effect)

As the second slit elastic members, dedicated elastic members may be provided, but the three-dimensional gather elastic members are preferably used.

<The Invention of Claim 5>

The disposable diaper according to any one of claims 1 to 4, wherein side flap parts are provided so as to protrude at the both sides in the width-direction of the absorber and plane gather elastic members are provided so as to extend in the front-back direction in the side flap parts, and at least portions of the plane gather elastic members crossing the second slits serve as the second slit elastic members.

(Operation and Effect)

As the second slit elastic members, dedicated elastic members may be provided but the plane gather elastic members are preferably used.

<The Invention of Claim 6>

The disposable diaper according to any one of claims 1 to 5, wherein the absorbent article includes, as the second slit elastic members, elastic members extending in the front-back direction so as to cross the second slits on at least one of the front side and back side.

(Operation and Effect)

Including the second slit elastic members in such a position allows their contraction force to be exerted directly on the second slits, thereby making favorable the action of deforming and keeping the deformation described above.

<The Invention of Claim 7>

The disposable diaper according to any one of claims 1 to 6, wherein the clearance width of the second slits is 3 to 8 mm.

(Operation and Effect)

When the clearance of the second slits is too narrow, the action of deforming is less effective, and when the clearance of the second slits is too wide, the second slits are widely open even in the deformed state described above to reduce liquid diffusibility in the direction crossing over the second slits. Accordingly, the clearance is preferably set within the foregoing range.

Advantageous Effects of Invention

As described above, according to the present invention, it is possible to provide the advantages of improving the liquid diffusibility and fit of the absorber having the first slit extending in the front-back direction and the second slits continuing laterally from the first slit to the side edges, and others.

DESCRIPTION OF EMBODIMENT

Figure 1:
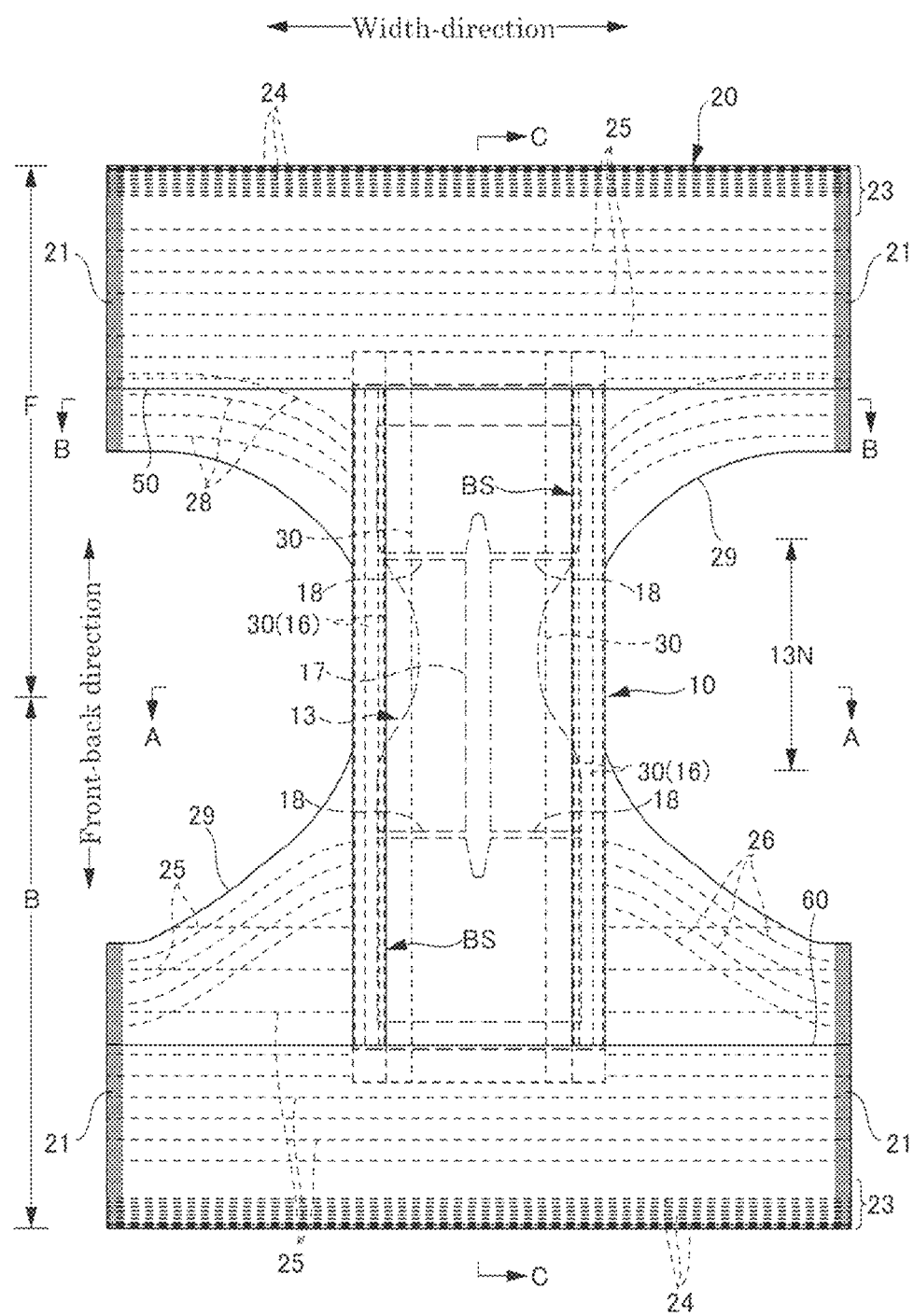
FIG. 1 is a plane view (inner surface side) of an underpants-type disposable diaper in a developed state.

One embodiment of the present invention will be described in detail with reference to the accompanied drawings. The "extension ratio" herein takes on a value relative to the natural length as 100%. The dot patterns in the drawings represent a joining means such as a hot-melt adhesive.

FIGS. 1 to 7 illustrate underpants-type disposable diaper. The underpants-type disposable diaper (hereinafter, also simply called diaper) has an outer body 20 constituting integrally a front panel F and a back panel B and an inner body 10 fixed to the inner surface of the outer body 20 ranging from the front panel F to the back panel B. The inner body 10 is formed by interposing an absorber 13 between a liquid pervious face sheet 11 and a liquid impervious back sheet 12. In manufacturing, the back surface of the inner body 10 is joined to the inner surface (upper surface) of the outer body 20 by a joining means such as a hot-melt adhesive (as illustrated in the dot-patterned part of FIG. 2), then the inner body 10 and the outer body 20 are folded in the center in the front-back (vertical) direction as a boundary between the front panel F and the back panel B, and then the both side parts are joined together by heat welding, a hot-melt adhesive, or the like to form side seal portions 21, thereby obtaining the underpants-type disposable diaper having a waist opening and a pair of right and left leg openings.

(Structure Example of the Inner Body)

Figure 4:
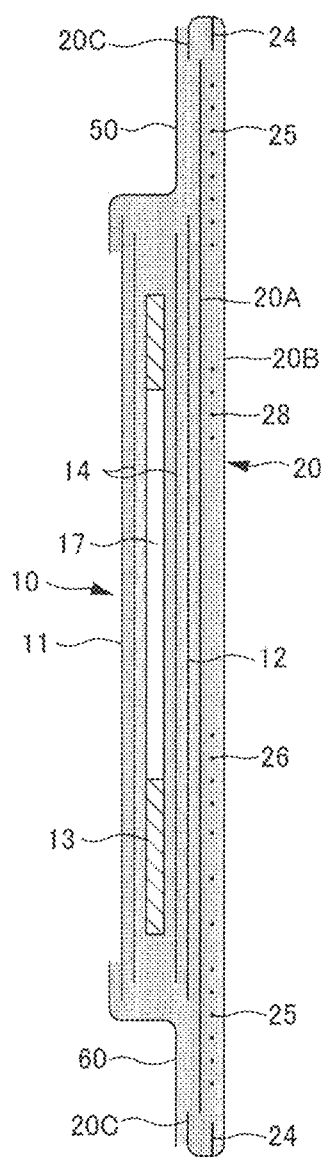
FIG. 4 is a cross-sectional view of FIG. 1 taken along line C-C.
Figure 5:
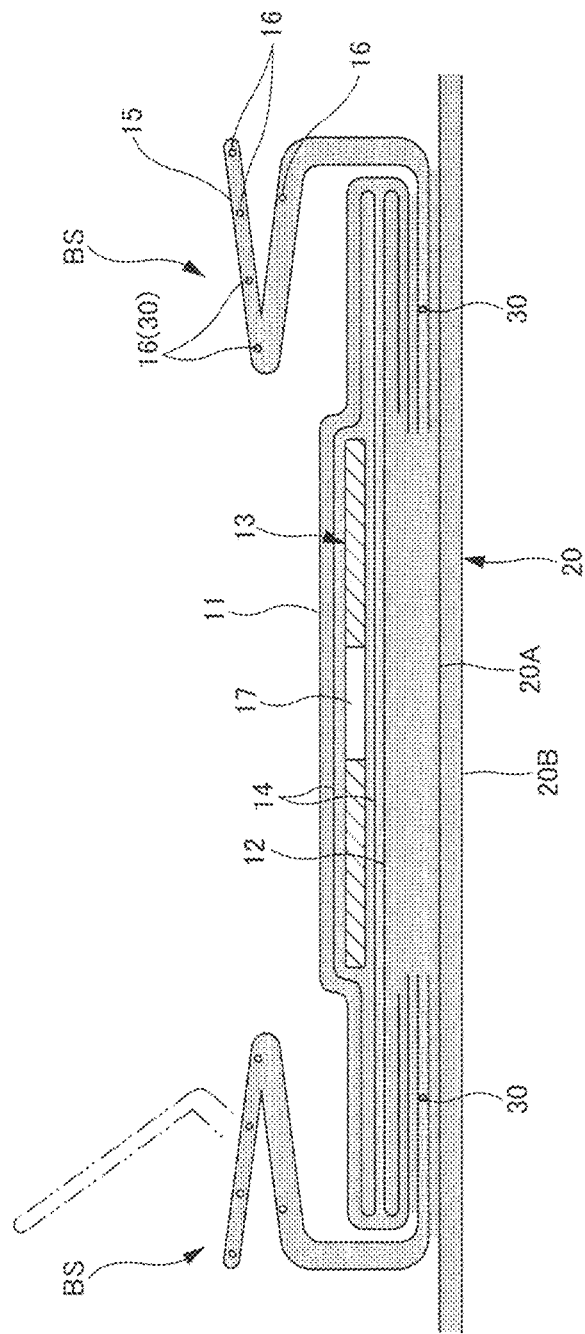
FIG. 5 is a cross-sectional view of FIG. 1 taken along line A-A.
Figure 6:
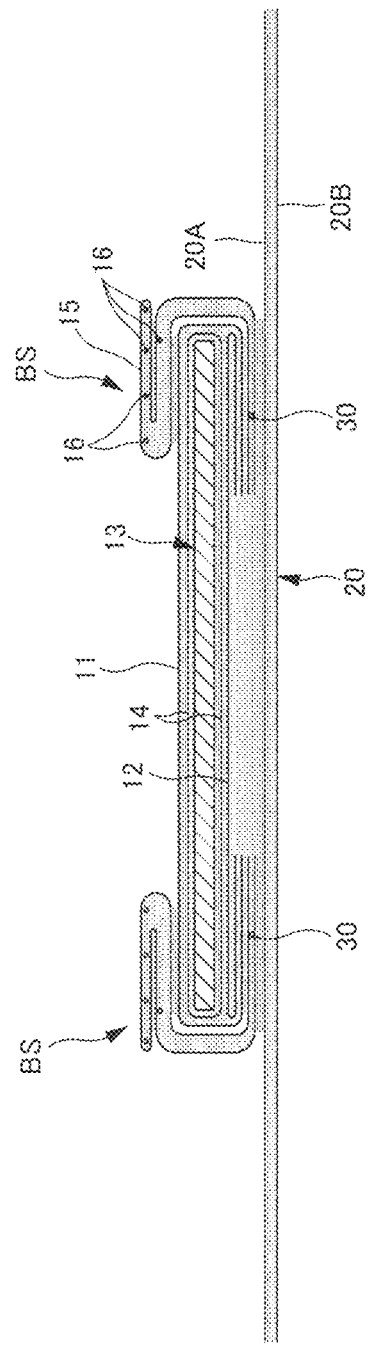
FIG. 6 is a cross-sectional view of FIG. 1 taken along line B-B.
Figure 7:
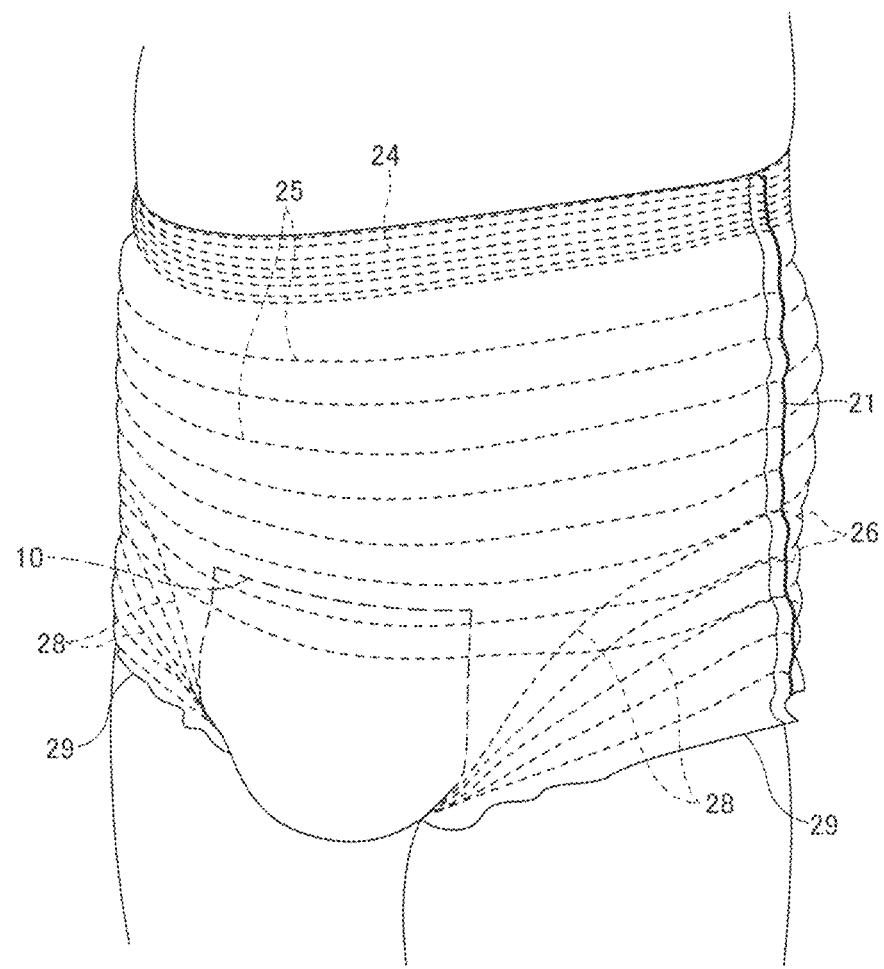
FIG. 7 is a plane view of the underpants-type disposable diaper in the worn state.

As illustrated in FIGS. 4 to 6, the inner body 10 is structured such that the absorber 13 is interposed between the liquid pervious face sheet 11 made of non-woven fabric or the like and the liquid impervious back sheet 12 made of polyethylene or the like. The inner body 10 is intended to absorb and hold excretion having passed through the face sheet 11. Although there is no particular limitation on the planar shape of the inner body 10, the inner body 10 is generally shaped in an approximate rectangle as in the illustrated drawing.

The liquid pervious face sheet 11 covering the external side (skin-contacting side) of the absorber 13 is preferably a porous or non-porous non-woven fabric sheet or a porous plastic sheet. The raw fibers for non-woven fabric may be synthetic fibers based on olefin such as polyethylene or polypropylene, or synthetic fibers based on polyester or polyamide, or reproduced fibers of rayon or cupra, natural fibers of cotton or the like. The non-woven fabric may be produced by any appropriate processing method such as spun-lacing, spun-bonding, thermal bonding, melt-blowing, or needle punching. Among these processing methods, the spun-lacing method is excellent for flexibility and drape properties, and the thermal bonding method is excellent for bulkiness and softness. Forming a large number of through holes in the liquid pervious face sheet 11 would allow quick absorption of urine and the like and produce an excellent feeling of dryness. The liquid pervious face sheet 11 wraps around the side edges of the absorber 13 and extends up to the back surface of the absorber 13.

The liquid impervious back sheet 12 covering the back side (non-skin-contacting side) of the absorber 13 is made of a liquid impervious plastic sheet of polyethylene, polypropylene, or the like. However, in recent years, the liquid impervious plastic sheets with moisture perviousness have been used preferably from the viewpoint of prevention of stuffiness. The liquid impervious and moisture pervious sheet is a microporous sheet that is obtained by melting and kneading an inorganic filling agent in an olefin resin such as polyethylene, polypropylene, or the like to form a sheet and then elongating the sheet in a uniaxial or biaxial direction, for example.

The absorber 13 is basically made from a publicly known material, for example, accumulated pulp fibers, a filament assembly of cellulose acetate or the like, or non-woven fabric. The absorber 13 may include as necessary high-absorbent polymer particles mixed and fixed thereto. The absorber 13 can be wrapped as necessary with a package sheet 14 with liquid perviousness and liquid retention such as crepe paper for retention of the shape and the polymer.

The absorber 13 is shaped as a whole like a sand glass with a narrower part 13N smaller in width than the front and back sides of the crotch portion. However, the absorber 13 may have an arbitrary shape such as a rectangle. The dimensions of the narrower part 13N can be decided as appropriate. However, the length in the front-back direction of the narrower part 13N can be about 20 to 50% of the entire length of the diaper. The smallest width of the narrower part 13N can be about 40 to 60% of the entire width of the absorber 13. When the planar shape of the inner body 10 is an approximate rectangle with the narrower part 13N as described above, in the inner body 10, remaining parts without the absorber 13 are formed according to the narrower part 13N of the absorber 13.

The inner body 10 has three-dimensional gathers BS fitting around the legs on the both sides. As illustrated in FIGS. 5 and 6, each of the three-dimensional gathers BS is formed with a three-dimensional gather sheet 15 as a two-folded duplicate sheet including a fixation portion fixed to the side of the back surface of the inner body, a main unit portion extending from the fixation portion through the lateral side of the inner body to the side part of the front surface of the inner body, lying down portions formed by fixing the front end and back end of the main unit portion in a lying down state to the side parts of the front surface of the inner body, and a free portion formed in an un-fixed state between the lying down portions. Water-repellent non-woven fabric is preferably used for the three-dimensional gather sheet 15.

Elongated three-dimensional gather elastic members 16 are arranged at forward ends of the free portion in the duplicate sheet. The three-dimensional gather elastic members 16 are intended to stand the free portions protruding from the side edges of the absorber by their elastic stretching force as illustrated by the two-dot chain line in FIG. 5 to form the three-dimensional gathers BS in the product state.

The liquid impervious back sheet 12 is folded back together with the liquid pervious face sheet 11 on the width-direction both sides of the absorber 13. The liquid impervious back sheet 12 is desirably opaque so as not to allow the dark color of stool and urine to be seen through. To make the liquid impervious back sheet 12 opaque, plastic is preferably formed into a film with internal addition of a mixture of pigments and fillers such as calcium carbonate, titanium oxide, zinc oxide, white carbon, clay, talc, and barium sulfate.

The gather elastic members 16 can be made from a generally used material such as styrene-based rubber, olefin-based rubber, urethane-based rubber, ester-based rubber, polyurethane, polyethylene, polystyrene, styrene-butadiene, silicon, or polyester. To make the gather elastic members 16 hard to see from the outside, it is preferable that the gather elastic members 16 have a thickness of 925 dtex or less and are arranged under a tension of 150 to 350% at intervals of 7.0 mm or less. The gather elastic members 16 may be a thread type as illustrated in the drawing or a tape type with a certain width.

As the liquid pervious face sheet 11, the raw fibers for the three-dimensional gather sheets 15 may be synthetic fibers based on olefin such as polyethylene or polypropylene, polyester, polyamide, or reproduced fibers of rayon or cupra, natural fibers of cotton or the like. The non-woven fabric may be produced by any appropriate processing method such as spun-bonding, thermal bonding, melt-blowing, or needle punching. However, in particular, the non-woven fabric with low basis weight and high air permeability is preferably used for the three-dimensional gather sheets 15 for prevention of stuffiness. Further, the three-dimensional gather sheets 15 are desirably made from water-repellent non-woven fabric coated with a silicon-based, paraffin metal-based, or alkyl electrochromic chloride-based water repellent agent to prevent passage of urine or the like and rash on the wearer's body, and enhance the feel and texture (feeling of dryness).

The outer body 20 has a two-layer structure composed of a pressing sheet 20A and a back sheet 20B made of non-woven fabric or the like as illustrated in FIGS. 4 to 6. Various elastic members are arranged between the pressing sheet 20A and the back sheet 20B and between the non-woven fabrics of folded portions 20C formed by folding the waist opening edges of the back sheet 20B toward the inner surface side to impart elasticity. The planar shape of the outer body 20 is an approximate sand glass as a whole due to concave leg lines 29 formed on the both sides of the intermediate portion to make the leg openings.

Figure 2:
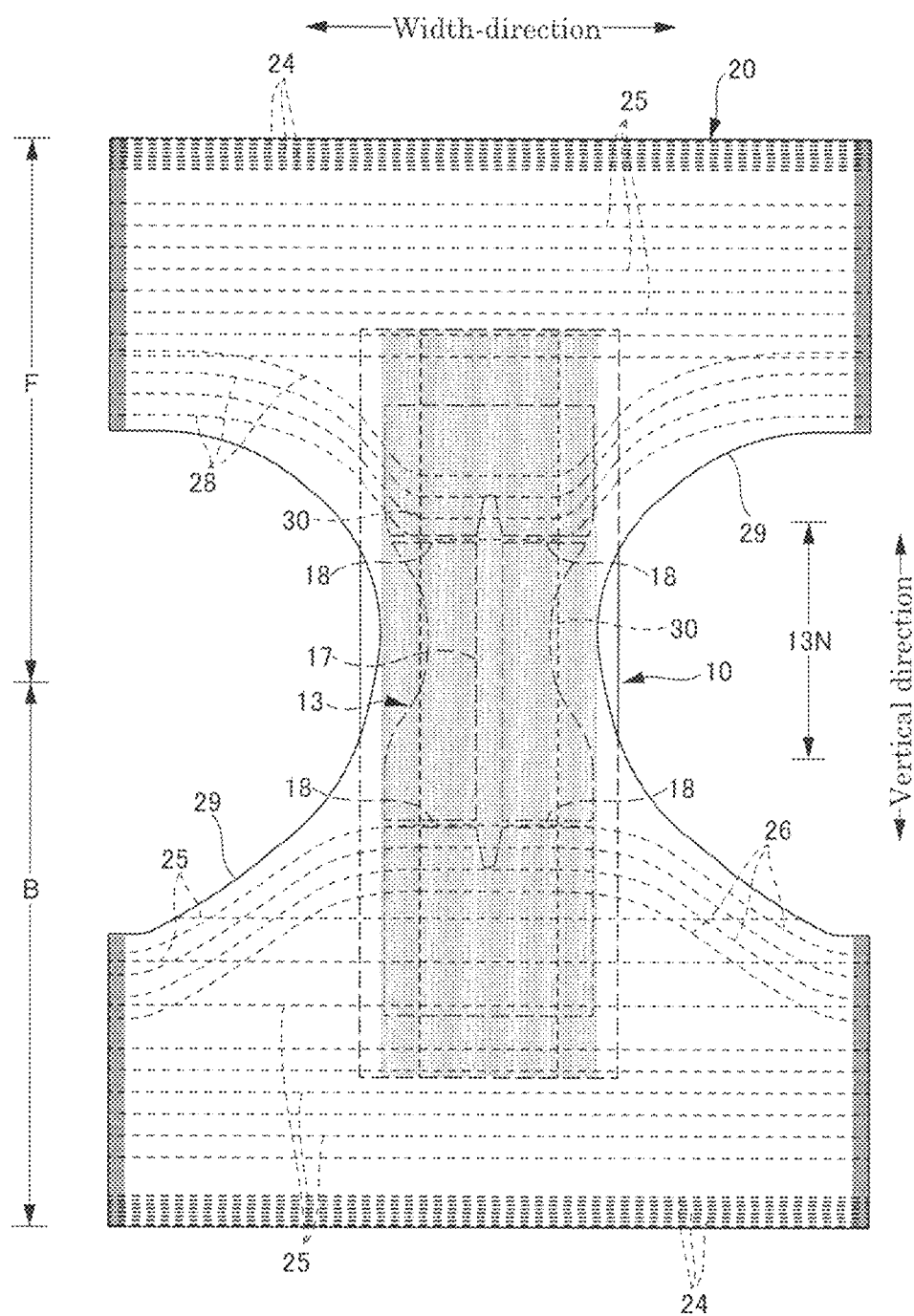
FIG. 2 is a plane view (outer surface side) of the underpants-type disposable diaper in the developed state.
Figure 3:
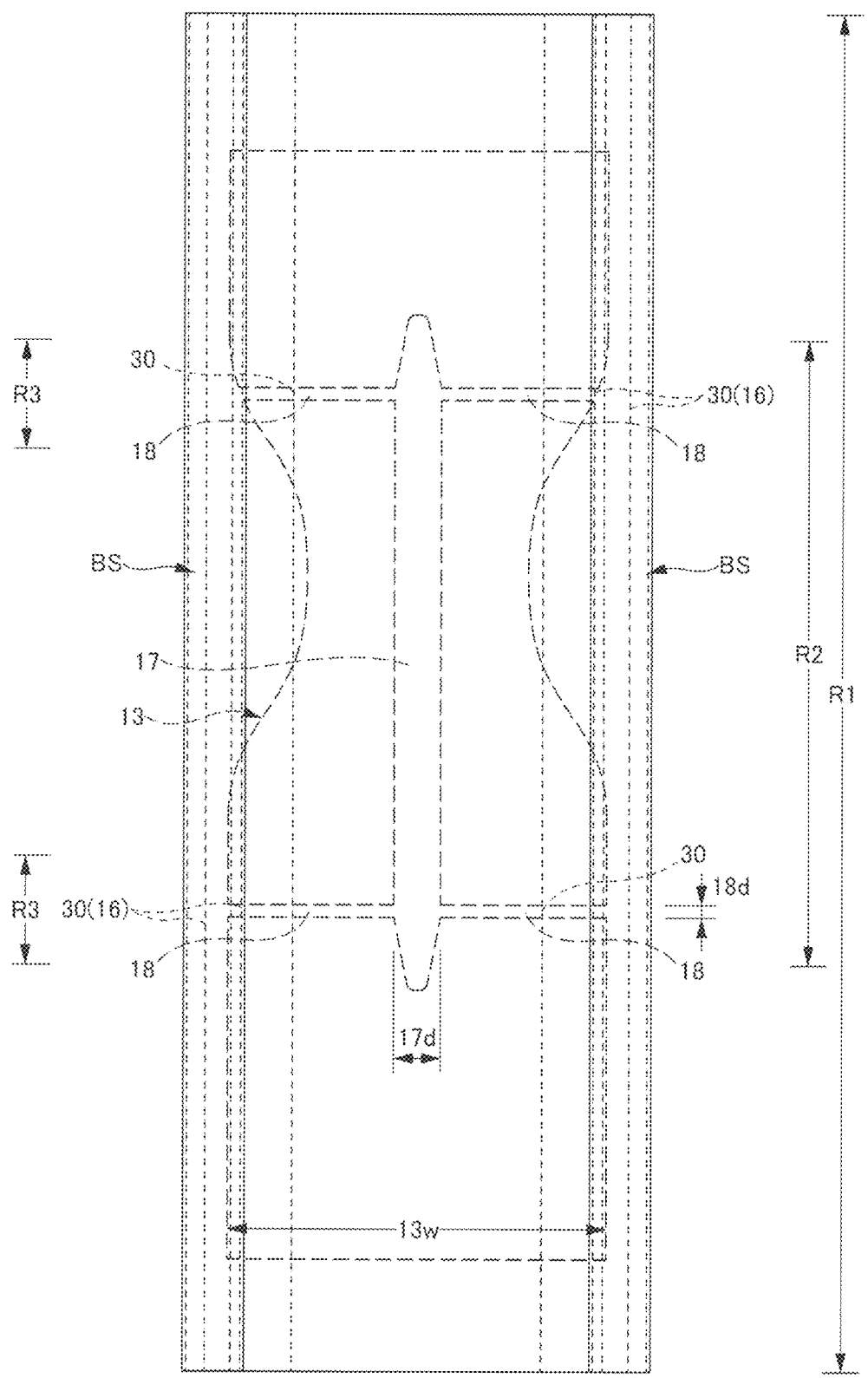
FIG. 3 is a plane view of main components of an absorber.

In the illustrated mode, the outer body 20 has, as elastic members, waist portion elastic members 24 arranged in waist opening neighborhoods 23 and a plurality of waist lower portion elastic members 25 arranged along a width direction at vertical intervals in the front panel F and the back panel B, in the developed state illustrated in FIGS. 1 to 3. Besides, separately from the waist lower portion elastic members 25, the outer body 20 includes a plurality of curved elastic members 26 and 28 that is arranged at intervals without crossing each other and is curved and extended in the front body F and the back panel B in a pattern ranging from one side seal portion 21 toward the crotch portion along one leg opening, crossing over the crotch portion, and reaching the other side seal portion 21 along the other leg opening. These elastic members 24 to 28 are fixed in the state extended at a predetermined stretch rate along their respective extending directions. The outer body 20 has no leg elastic members that continue from the side seal portions of the front panel F to the side seal portions of the back panel B along the leg lines 29.

The waist portion elastic members 24 are a plurality of elongated elastic members such as rubber threads arranged at vertical intervals in the waist opening edge neighborhood in the zones of the side seal portions 21 where the front panel F and the back panel B are joined together, and are intended to elastically tighten the wearer's waist to exert a stretching force and attach the diaper to the wearer's body. The waist portion elastic members 24 are rubber threads in the illustrated example but may be tape-like stretch members, for example. In addition, the waist portion elastic members 24 are sandwiched in the non-woven fabric of the folded portions 20C of the back sheet 20B at the waist portion in the illustrated example. Alternatively, the waist portion elastic members 24 may be sandwiched between the pressing sheet 20A and the back sheet 20B.

The waist lower portion elastic members 25 are elongated elastic members such as rubber threads arranged at vertical intervals in the zones of the side seal portions 21 ranging generally from the upper to lower sides, and are intended to exert a width-direction stretching force to the waist portions of the front panel F and the back panel B and closely attach the diaper to the wearer's body. No clear differentiation may be made between the waist portion elastic members 24 and the waist lower portion elastic members 25. For example, of the elastic members arranged in the width direction at vertical intervals in the front panel F and the back panel B, some of the upper-side elastic members may serve as waist portion elastic members, although the number of the waist portion elastic members cannot be specified, and the remaining elastic members may serve as waist lower portion elastic members.

The dorsal-side curved elastic members 26 disposed separately from the waist lower portion elastic members 25 in the back panel B are elongated elastic members such as rubber threads that are arranged along predetermined curve lines. The number of the dorsal-side curved elastic member 26 may be one but is preferably plural. In the illustrated example, the dorsal-side curved elastic members 26 are four elongated elastic members such as rubber threads. These dorsal-side curved elastic members 26 are arranged at intervals without crossing each other. The dorsal-side curved elastic members 26 are not arranged as a substantially single bundle of about two or three elastic members at close intervals but three or more, preferably four or more elastic members are arranged at intervals of about 3 to 20 mm, preferably about 6 to 16 mm to form a predetermined stretchable zone.

The ventral-side curved elastic members 28 disposed separately from the waist lower portion elastic member group 25 in the front panel F of the outer body 20 are elongated elastic members such as rubber threads and are arranged along predetermined curved lines. The number of the ventral-side curved elastic member 28 may be one but is preferably plural. In the illustrated example, the ventral-side curved elastic members 28 are four thread-like elastic members. These ventral-side curved elastic members 28 are arranged at intervals without crossing each other. The ventral-side curved elastic members 28 are not arranged as a substantially single bundle of about two or three elastic members at close intervals but three or more, preferably four or more elastic members are arranged at intervals of about 3 to 20 mm, preferably about 6 to 16 mm to form a predetermined stretchable zone.

Figure 8:
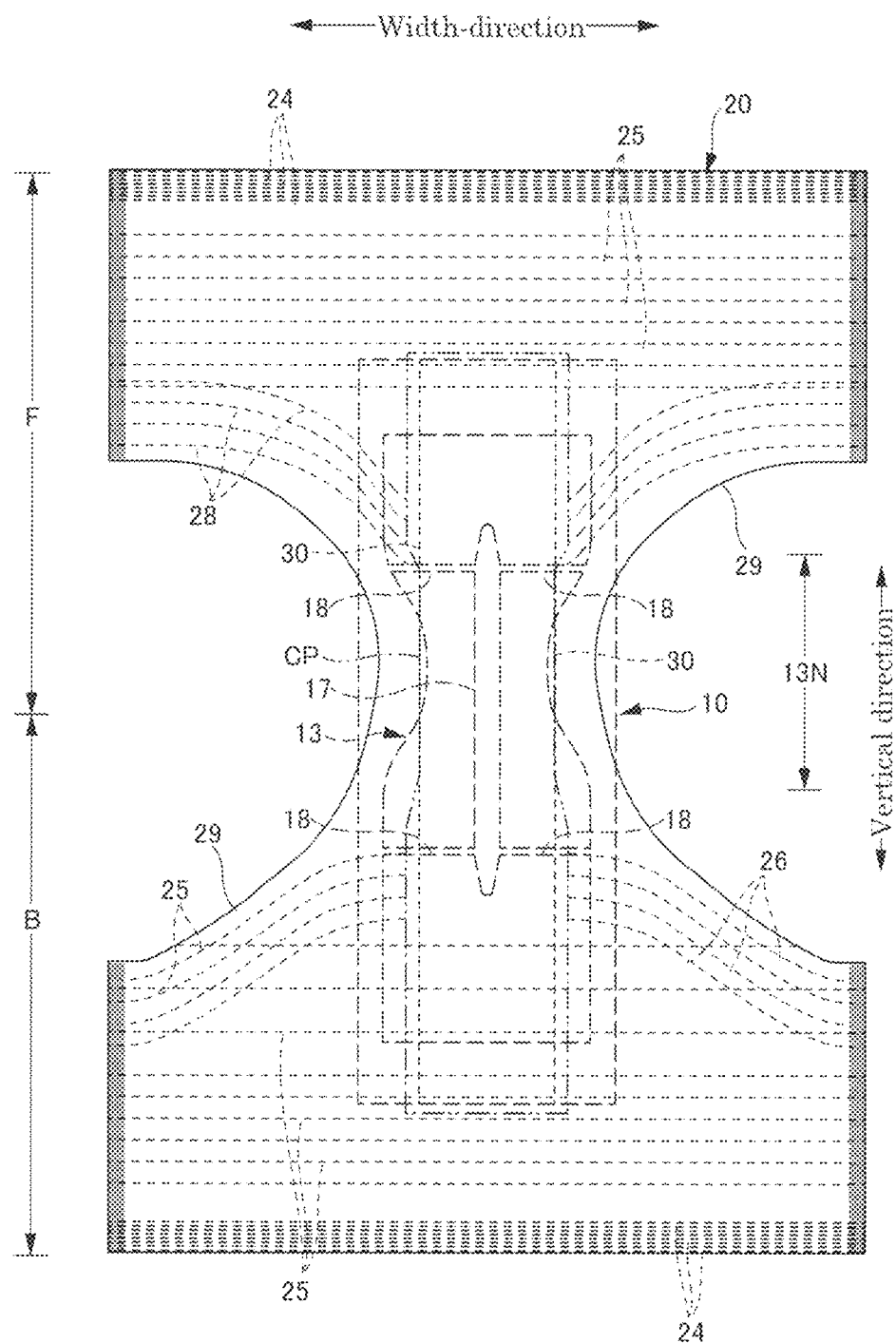
FIG. 8 is a plane view of a cut pattern for elastic members.

In addition, as understood from FIG. 8 described later, after the waist lower portion elastic members 25 and the curved elastic members 26 and 28 are arranged in the front panel F and the back panel B and are continuously fixed to the outer body at the time of manufacture, some or all of the elastic members overlapping the inner body may be finely cut in a predetermined cutting pattern CP to form a non-contraction part on which no contraction force acts (that is, the part overlapping the cutting pattern CP in FIG. 8), and form parts extending laterally from the non-contraction part as contraction parts on which a contraction force acts (that is, the parts where the waist lower portion elastic members 25 and the curved elastic members 26 and 28 are left continuously on the sides more lateral than the cutting pattern CP in FIG. 8). Accordingly, after being continuously provided from one side seal portion 21 to the other (opposite) side seal portion 21 crossing over the inner body 10, some or all of the waist lower portion elastic members 25 and the curved elastic members 26 and 28 overlapping the inner body 10 are finely cut. This prevents unnecessary width-direction contraction of the inner body (especially the absorber 13). As a matter of course, the waist lower portion elastic members 25 and the curved elastic members 26 and 28 may be arranged continuously crossing over the inner body 10.

The outer body 20 can be manufactured by the technique described in JP-A No. 4-28363 or JP-A No. 11-332913, for example. In addition, the curved elastic members 26 and 28 can be preferably cut and made discontinuous on the inner body 10 by employing the cutting technique described in JP-A No. 2002-35029, JP-A No. 2002-178428, or JP-A No. 2002-273808.

Unlike in the illustrated example, the curved elastic members 26 and 28 may be provided only in either of the front panel F and the back panel B. When the curved elastic members 26 and 28 are provided in both the front panel F and the back panel B, some or all of the group of curved elastic members 28 arranged in the front panel F and some or all of the group of curved elastic members 26 arranged in the back panel B may cross each other (not illustrated). However, in a preferred mode, the group of curved elastic members 28 arranged in the front panel F and the group of curved elastic members 26 arranged in the back panel B do not cross each other, but separate from each other in the vertical direction at the intermediate portion in the front-back direction, in particular, at the position slightly closer to the front panel F.

Further, the curved elastic members 26 and 28 may not be curved entirely but may have linear parts.

The extension ratios of the elastic members 24 to 28 in attaching can be decided as appropriate. However, for a general diaper for adults, the extension ratio of the waist portion elastic members 24 can be about 160 to 320%, the extension ratio of the waist lower portion elastic members 25 can be about 160 to 320%, and the extension ratio of the curved elastic members 26 and 28 can be about 230 to 320%.

(Front and Back Pressing Sheets)

As also illustrated in FIGS. 1 and 4, front and back pressing sheets 50 and 60 may be provided to cover the front and back end portions of the inner body 10 on the inner surface of the outer body 20 and prevent leakage from the front and back edges of the inner body 10. The illustrated mode will be described more in detail. The front pressing sheet 50 extends on the inner surface of the front panel F in the width direction entirely from the inner surface of the folded portion 20C at the waist-side end to the part overlapping the front end part of the inner body 10. The back pressing sheet 60 extends on the inner surface of the back panel B in the width direction entirely from the inner surface of the folded portion 20C at the waist-side end to the part overlapping the back end part of the inner body 10. The front and back pressing sheets 50 and 60 can have small non-bonded portions at the entire crotch lower side edges in the width direction (or only at the central portion) to prevent the adhesive from squeezing out and allow the non-bonded portions to lift slightly from the face sheet and serve as leak prevention walls.

Attaching the front and back pressing sheets 50 and 60 as separate members as in the illustrated mode would provide the advantage of a higher degree of freedom of material selection but also provide the disadvantage of increase in the numbers of materials and manufacturing processes. Accordingly, the folded portions 20C formed by folding the outer body 20 toward the inside of the diaper may be extended up to the parts overlapping the inner body 10 to form the parts equivalent to the pressing sheets 50 and 60.

(About the Slits in the Absorber)

Figure 9:
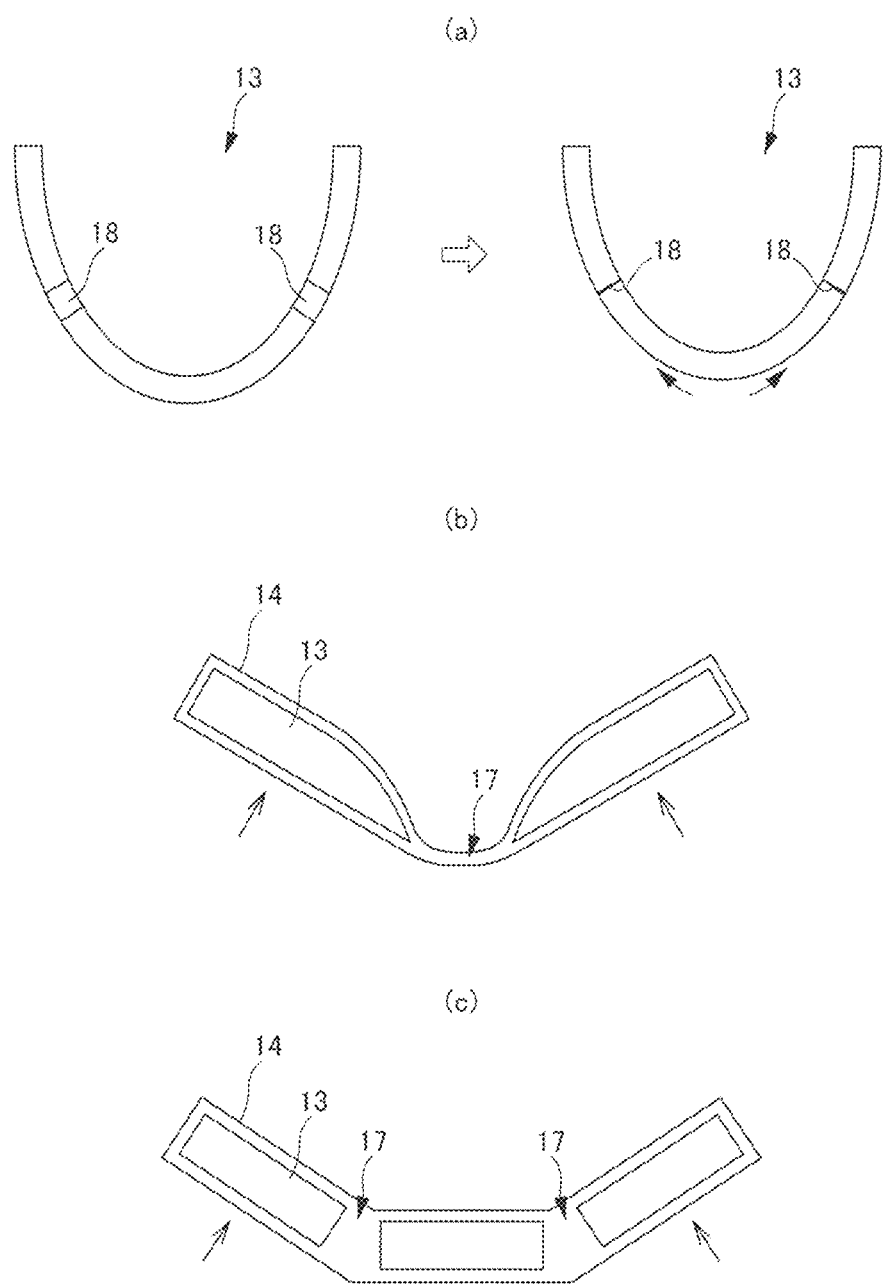
FIG. 9(*a*) is a schematic vertical cross-section view illustrating a change from the state before closing of second slits to the state after closing of the second slits, and FIGS. 9(*b*) and 9(*b*) are lateral cross-sectional views of the absorber.

Characteristically, as illustrated in FIGS. 1 to 5, one first slit 17 extending in the front-back direction is formed in the width-direction intermediate portion of the absorber 13, second slits 18 continuing from the front end side and back end side of the first slit 17 to the side edges on the width-direction both sides, and second slit elastic members 30 cross the direction of continuance of the second slits 18 and exert a contraction force in the direction of closing of the second slits 18. Accordingly, in the absorber 13 of the embodiment, the second slits 18 are partially or completely closed as illustrated in FIG. 9(a) by the contraction force of the second slit elastic members 30 to shorten the front-back direction lengths of the width-direction both sides of the first slit 17, and the second slits 18 are folded along the first slit 17 as illustrated in FIGS. 9(b) and 9(c) to make the absorber 13 deformed in an almost boat shape. Therefore, the widths of the second slits 18 are smaller or the both sides of the second slits 18 are brought into contact with each other to make favorable liquid diffusibility in the direction crossing over the second slits 18 and suppress the liquid diffusibility in the direction along the second slits 18, thereby to enhance the effect of preventing lateral leakage. In addition, the absorber 13 is deformed in a boat shape as a whole by combination of the actions of deformation of the first slit 17 and the second slits 18 to improve the fit and the leakage prevention effect.

Figure 10:
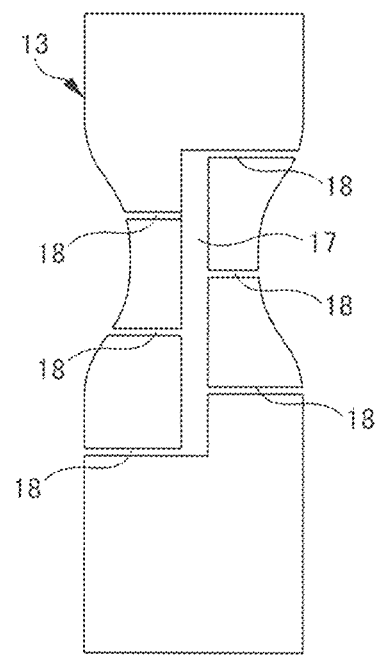
FIG. 10 is a plane view of the absorber.
Figure 12:
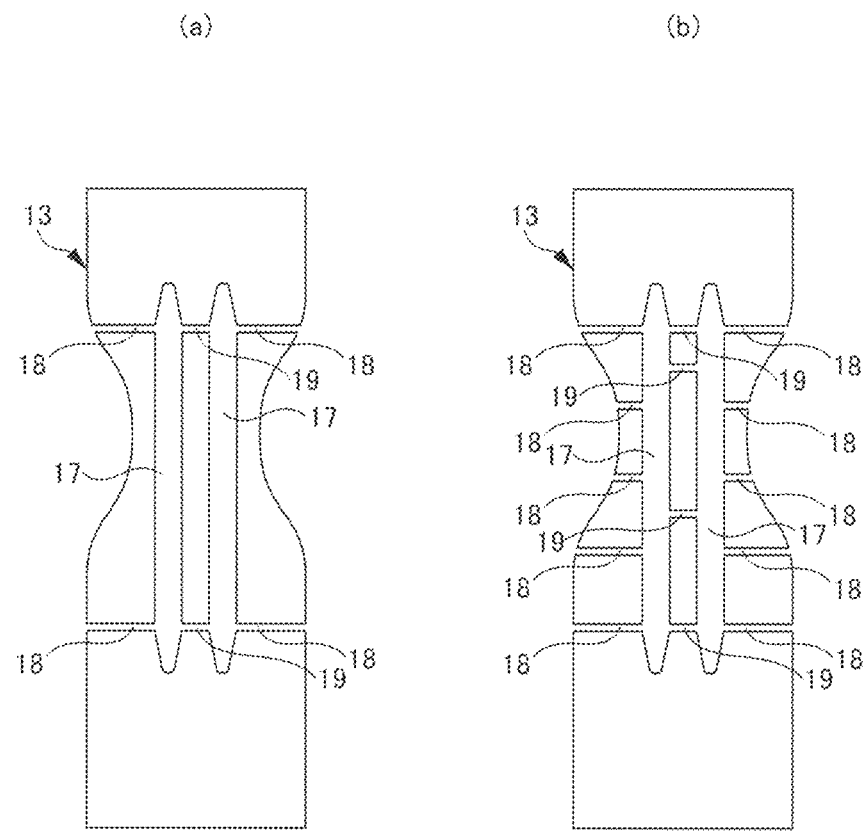
FIGS. 12(*a*) and 12(*b*) are plane views of the absorber.

The number of the second slits 18 needs to be two or more (front and back ones) on one side in the width-direction. However, three or more second slits 18 may be provided at front-back direction intervals as illustrated in FIGS. 10 and 12(b). Alternatively, the front-back direction positions of the second slits 18 may be bilaterally symmetric or may be bilaterally asymmetric as illustrated in FIG. 10.

Two first slits 17 may be provided at a width-direction interval as illustrated in FIGS. 11(a), 11(b), 12(a), and 12(b). In that case, the second slits 18 include ones continuing from the first slit 17 on one side in the width-direction to the side edge of the absorber 13 on one side in the width-direction, and ones continuing from the first slit 17 on the other side in the width-direction to the side edge of the absorber 13 on the other side in the width-direction. When the two first slits 17 are provided as described above, the regions of the second slits 18 rise with respect to the region between the first slits 17 to turn the absorber into a boat shape. This provides a more favorable fit. Three or more first slits 17 may be provided. In conclusion, the second slits 18 are continuously provided from the front end side and back end side of a first slit formation region (that is, in the case of one first slit 17, the region of the first slit 17 is applied, and in the case of a plurality of first slits 17, the region including the both slits on the most lateral sides and the space between them is applied) to the side edges on the width-direction both sides.

Figure 11:
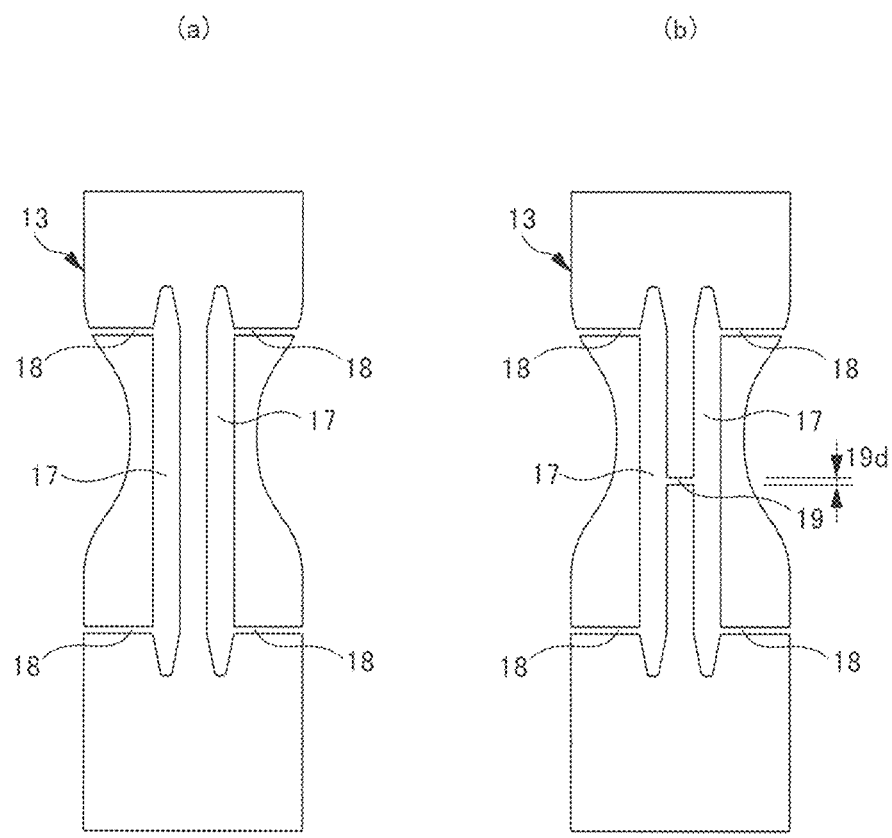
FIGS. 11(*a*) and 11(*b*) are plane views of the absorber.

When two first slits 17 are provided, they may not be necessarily connected in the width direction as illustrated in FIG. 11(a) but a cross-linkage slit 19 is preferably provided to link the first slits 17 as illustrated in FIGS. 11(b), 12(a), and 12(b). This allows linkage of the two first slits 17 and the second slits 18 on the width-direction both sides of the first slits 17. Accordingly, in the mask at the time of manufacture described above, the main slit pattern can be supported from the width-direction both sides via the auxiliary slit pattern (the pattern for forming the second slits 18 and the cross-linkage slit 19), which allows the main slit pattern to be supported more firmly. In addition, when the cross-linkage slit 19 as described above is provided, setting sum total 19d of clearance width of the cross-linkage slit 19 to be smaller than the sum total of clearance width 18d of the second slits 18 allows the absorber to be likely to be turned into a boat shape described above.

The clearance width 18d of the second slits 18 can be decided as appropriate. However, when the clearance width 18d of the second slits 18 is too narrow, the action of deforming is less effective, and when the clearance width 18d of the second slits 18 is too wide, the second slits 18 are widely open even in the deformed state described above to reduce liquid diffusibility in the direction crossing over the second slits 18. Accordingly, the clearance width 18d of the second slits 18 is preferably about 3 to 8 mm, in particular, about 3 to 5 mm. In addition, the clearance width 18d of the second slits 18 is desirably smaller than the clearance width 17d of the first slits 17 but the opposite may be accepted. Further, the clearance width 17d of the first slits 17 and the clearance width 18d of the second slits 18 may be increased or decreased depending on the positions in the direction of continuation.

Figure 16:
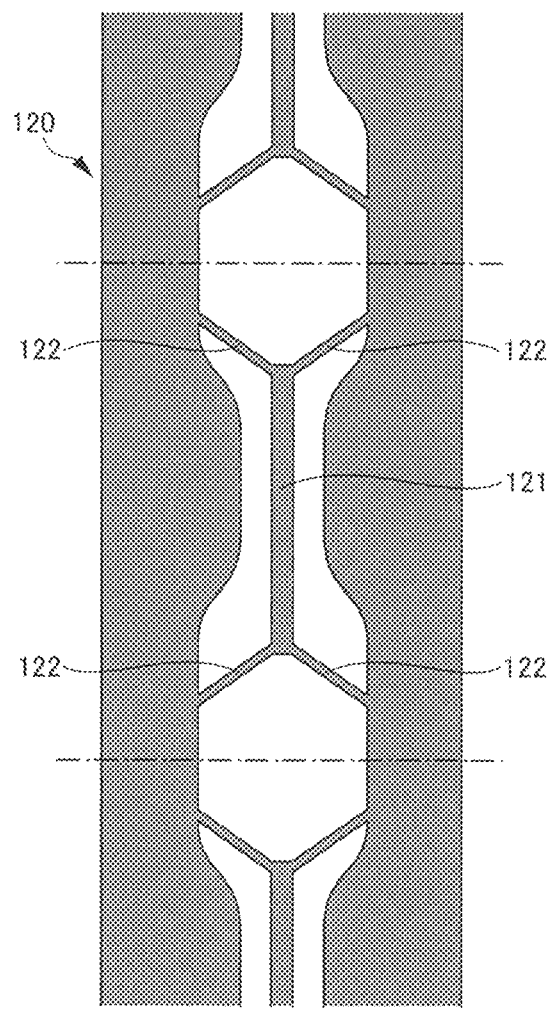
FIG. 16 is a plane view of an developed fiber-stacked mask.

The first slits 17 and the second slits 18 are linearly extended in the illustrated mode but may be extended in a curve. In addition, the second slits 18 may be provided along the width direction or may be obliquely provided in such a manner as to be positioned nearer the front-back direction end side (or the front-back direction central side in contrast) with increasing proximity to the lateral sides as seen from the pattern of mask illustrated in FIG. 16). Even when the first slits 17 are inclined with respect to the front-back direction, this falls within the range of "extending in the front-back direction" according to the present invention.

There is no limitation on the position of the first slit formation region as far as it is provided in the width-direction intermediate portion of the absorber 13. In general, however, the first slit formation region is desirably positioned in the width-direction center of the absorber 13, and the width of the first slit formation region (in the case of one first slit, its width 17d is applied) is desirably 5 to 20% of entire width 13w of the absorber 13. In addition, the front-back length of the first slit can be decided as appropriate and may be about 30 to 70% of the entire length of the absorber 13, for example. The position of the first slit 17 can be decided as appropriate depending on the diaper size. In a general case, however, when the front end position of the absorber 13 is assumed as 0% and the back end position of the absorber 13 as 100%, the first slit 17 is preferably in the position of 10 to 27%, in particular, 12 to 25%.

The connections between the second slits 18 and the first slit 17 are positioned on the front end side and back end side of the first slit 17. Since the connections are preferably positioned closer to the front side and the back side of the first slit 17, the connections are desirably positioned in the front end portion and the back end portion of the first slit 17 as in the illustrated mode. In addition, the second slits 18 are preferably positioned closer to the front and back sides from the viewpoint of leakage prevention, and in particular, the second slits 18 are desirably positioned closer to the front and back end portions of the narrower part 13N of the absorber or closer to the front and back sides of the narrower part 13N of the absorber.

For the second slit elastic members 30, some or all of elastic members provided for other purposes or dedicated elastic members may be provided as far as they cross the direction of continuance of the second slits 18 and exert a contraction force in the direction of closing of the second slits 18. The second slit elastic members 30 are desirably orthogonal to the direction of continuance of the second slits 18 but may be inclined with respect to the orthogonal direction as far as they exert a contraction force in the direction of closing of the second slits 18.

To transfer the action of contraction by the second slit elastic members 30 more effectively to the second slits 18, the second slit elastic members 30 are preferably provided more outside than the width-direction centers of the second slits 18, and in particular, they are more preferably provided in sections overlapping the side ends of the second slits 18 or more outside.

The mode illustrated in FIGS. 1 to 7 includes the three-dimensional gather elastic members 16 that cross the direction of continuance of the second slits 18 and exert a contraction force in the direction of closing of the second slits 18. Accordingly, the three-dimensional gather elastic members 16 serve as the second slit elastic members 30. In addition, the dedicated second slit elastic members 30 are provided extending in the front-back direction to cross the second slits 18 on the back side of the absorber 13 on the right and left sides of the first slit 17. The three-dimensional gather elastic members 16 exert a less strong contraction force on the second slits 18 but they are essential members in the current disposable diaper and their positions with respect to the second slits 18 are preferable. Meanwhile, the dedicated second slit elastic members 30 extending in the front-back direction to cross the second slits 18 on the back side of the absorber 13 exert a contraction force directly on the second slits 18 and are preferably excellent in the action of deforming and keeping the deformation as described above. In the illustrated mode, the second slit elastic members 30 are provided in the three-dimensional gather sheet 15 in the fixation part fixed to the back surface of the inner body 10. Alternatively, the second slit elastic members 30 may be provided between the back surface of the inner body 10 and the three-dimensional gathers BS, or between the inner body 10 and the outer body 20. In contrast, the second slit elastic members 30 may be provided on the front side of the absorber 13, for example, between the face sheet 11 and the absorber 13.

Figure 13:
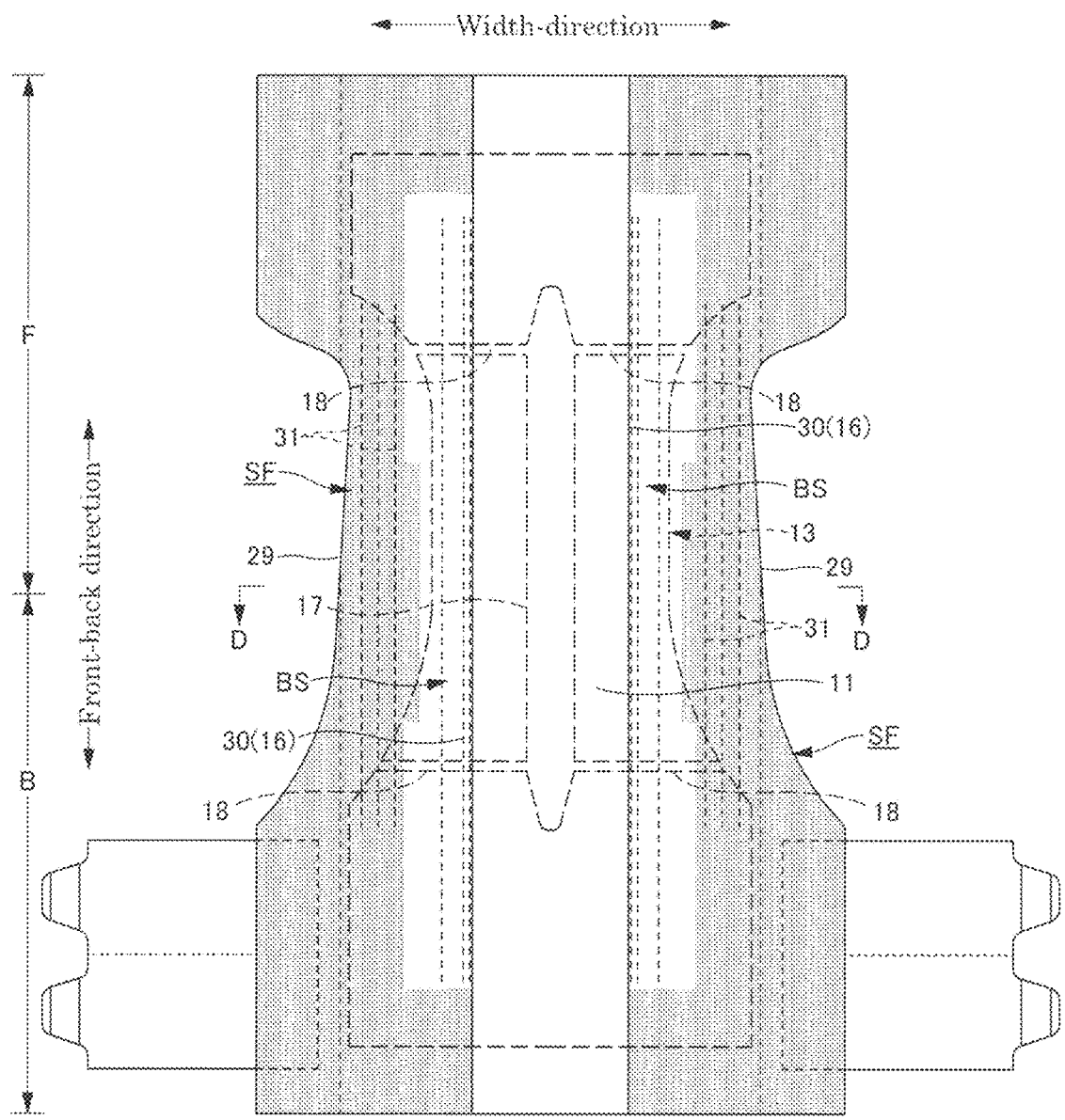
FIG. 13 is a plane view (inner surface side) of a tape-type disposable diaper in a developed state.
Figure 14:
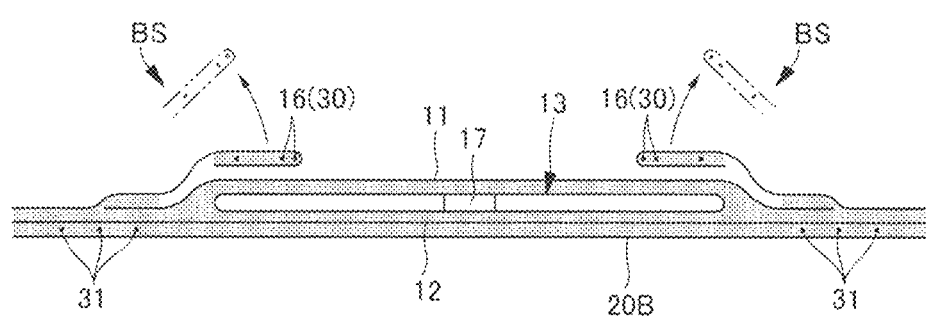
FIG. 14 is a cross-sectional view of FIG. 13 taken along line D-D.
Figure 15:
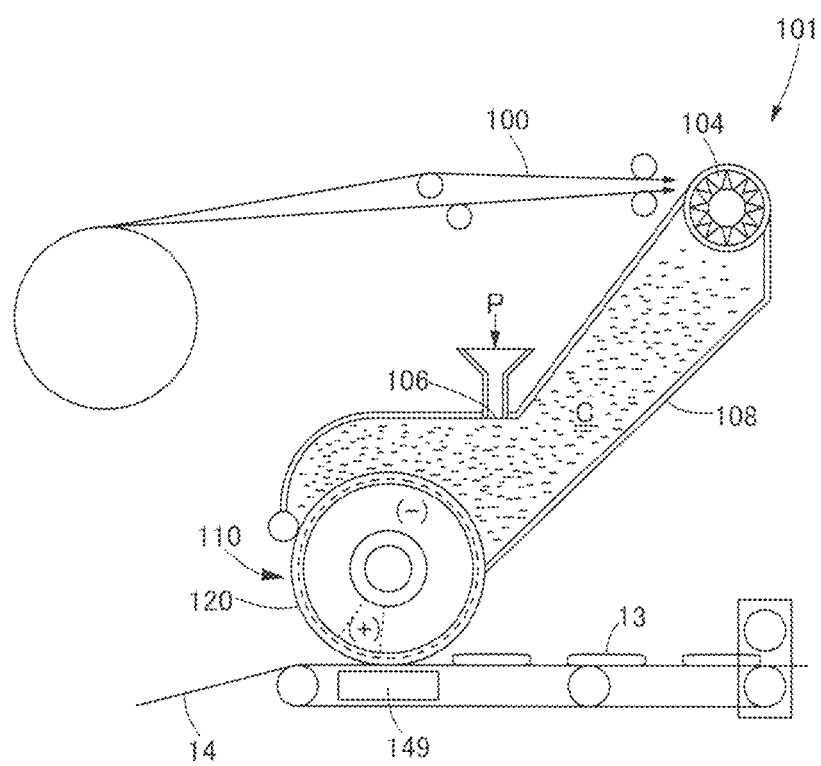
FIG. 15 is a schematic view of a fiber stacking apparatus for the absorber.

In most cases, the tape-type disposable diaper illustrated in FIGS. 13 and 14 or a large-sized pad-type disposable diaper not illustrated have side flap portions SF protruding to the width-direction both sides of the absorber 13 and plane gather elastic members 31 extending from the side flap portions SF in the front-back direction. Accordingly, in another preferable mode, the plane gather elastic members 31 cross the direction of continuance of the second slits 18 to serve as the second slit elastic members 30. The tape-type disposable diaper also includes the three-dimensional gather elastic members 16 that cross the direction of continuance of the second slits 18 and exert a contraction force in the direction of closing of the second slits 18, and the three-dimensional gather elastic members 16 also serve as the second slit elastic members 30. The other components of the tape-type disposable diaper are basically the same as those of the underpants-type disposable diaper and descriptions thereof will be omitted with the same reference signs as those of the underpants-type disposable diaper in FIGS. 13 and 14 to given thereto.

The range on which the front-back direction contraction force of the second slit elastic members 30 acts may be set as a range R1 including the front-back direction whole of the absorber 13 or as partial front-back direction ranges R2 and R3 containing the second slits 18. In the latter case, the integral contraction force exertion range R2 may be provided for the plurality of second slits 18 or the individual contraction force exertion ranges R3 may be provided for the individual second slits 18. The technique for setting the contraction force exertion ranges of the second slit elastic members 30 as the partial front-back direction ranges R2 and R3 containing the second slits 18 includes providing the second slit elastic members 30 only in the relevant ranges and providing the second slit elastic members in a wider range including the relevant ranges and finely cutting the second slit elastic members 30 in ranges other than the contraction force exertion range to remove elasticity.

INDUSTRIAL APPLICABILITY

The present invention is suited to pants-type disposable diapers in the foregoing example but is also applicable to various disposable diapers such as tape-type and pad-type disposable diapers and other general absorbent articles such as sanitary napkins.

REFERENCE SIGNS LIST

B Back panel
BS Three-dimensional gather
F Front panel
SF Side flap portion
10 Inner body
11 Face sheet
12 Liquid impervious back sheet
13 Absorber
13N Narrower part
14 Package sheet
15 Three-dimensional gather sheet
16 Three-dimensional gather elastic member
17 First slit
18 Second slit
19 Cross-linkage slit
20 Outer body
20C Folded portion
21 Side seal portion
24 Waist portion elastic member
25 Waist lower portion elastic member
26 and 28 Curved elastic member
26 Dorsal-side curved elastic member
28 Ventral-side curved elastic member
29 Leg line
30 Second slit elastic member
31 Plane gather elastic member

The invention claimed is:

1. A disposable diaper, wherein
an absorbent article includes an absorber,
the absorber has a first slit formation region in a width-direction intermediate portion where one or more first slits extending in a front-back direction are provided at width-direction intervals,
the absorber has second slits continuing from each of front end side and back end side of the first slit formation region toward width-direction both sides to side edges,
the absorbent article has second slit elastic members comprising elastic members, wherein the elastic members are provided on a back surface of the absorber, the elastic members cross the second slits, extend in the front-back direction, and exert a contraction force in the front-back direction to close the second slits,
a duplicate sheet including a fixation portion fixed to the absorber, is provided on the back surface of the absorber, and
the elastic members are fixed between the duplicate sheet in the fixation portion.

2. The disposable diaper according to claim 1, wherein the first slit formation region is composed of the two first slits provided at a width-direction interval, and
the second slits comprise slits continuing from the first slit on one side in the width-direction to the side edge of the absorber on one side in the width-direction and slits continuing from the first slit on an opposite side in the width-direction to the side edge of the absorber on the opposite side in the width-direction.

3. The disposable diaper according to claim 1, comprising a cross-linkage slit linking the two first slits in the width direction, wherein
the sum total of clearance width of the cross-linkage slit is smaller than the sum total of clearance width of the second slits.

4. The disposable diaper according to claim 1, wherein the clearance width of the second slits is 3 to 8 mm.

5. The disposable diaper according to claim 1, wherein the second slits are perpendicular to the first slits.

* * * * *